(12) United States Patent
Le Neel et al.

(10) Patent No.: US 10,557,812 B2
(45) Date of Patent: Feb. 11, 2020

(54) GAS SENSORS

(71) Applicant: STMICROELECTRONICS PTE LTD, Singapore (SG)

(72) Inventors: Olivier Le Neel, Singapore (SG); Alexandre Le Roch, Singapore (SG); Ayoub Lahlalia, Singapore (SG); Ravi Shankar, Singapore (SG)

(73) Assignee: STMICROELECTRONICS PTE LTD, Singapore (SG)

(*) Notice: Subject to any disclaimer, the term of this patent is extended or adjusted under 35 U.S.C. 154(b) by 0 days.

(21) Appl. No.: 15/367,081

(22) Filed: Dec. 1, 2016

(65) Prior Publication Data

US 2018/0156747 A1    Jun. 7, 2018

(51) Int. Cl.
*G01N 27/18* (2006.01)
*G01N 33/00* (2006.01)

(52) U.S. Cl.
CPC ......... *G01N 27/18* (2013.01); *G01N 33/0047* (2013.01)

(58) Field of Classification Search
CPC ............................ G01N 27/18; G01N 33/0047
USPC .......................................................... 422/98
See application file for complete search history.

(56) References Cited

U.S. PATENT DOCUMENTS

| | | |
|---|---|---|
| 4,608,232 A | 8/1986 | Sunano et al. |
| 4,938,053 A | 7/1990 | Jepson et al. |
| 5,834,777 A | 11/1998 | Wong |
| 6,111,280 A * | 8/2000 | Gardner ............... G01N 27/128 |
| | | 257/253 |

(Continued)

FOREIGN PATENT DOCUMENTS

| | | |
|---|---|---|
| CN | 1684285 A | 10/2005 |
| CN | 1732383 A | 2/2006 |

(Continued)

OTHER PUBLICATIONS

Allen et al., "Associations of Cognitive Function Scores with Carbon Dioxide, Ventilation, and Volatile Organic Compound Exposures in Office Workers: A Controlled Exposure Study of Green and Conventional Office Environments," *Environmental Health Perspectives* 124(6):805-812, Jun. 2016.

(Continued)

*Primary Examiner* — Sean E Conley
*Assistant Examiner* — Jacqueline Brazin
(74) *Attorney, Agent, or Firm* — Seed IP Law Group LLP

(57) ABSTRACT

The present disclosure is directed to a gas sensor that includes an active sensor area that is exposed to an environment for detection of elements. The gas sensor may be an air quality sensor that can be fixed in position or carried by a user. The gas sensor includes a heater formed above chamber. The gas sensor includes an active sensor layer above the heater that forms the active sensor area. The gas sensor can include a passive conductive layer, such as a hotplate that further conducts and distributes heat from the heater to the active sensor area. The heater can include a plurality of extensions. The heater can also include a first conductive layer and a second conductive layer on the first conductive layer where the second conductive layer includes a plurality of openings to increase an amount of heat and to more evenly distribute heat from the heater to the active sensor area.

26 Claims, 11 Drawing Sheets

(56) References Cited

U.S. PATENT DOCUMENTS

| | | |
|---|---|---|
| 6,243,474 B1 | 6/2001 | Tai et al. |
| 6,322,247 B1 | 11/2001 | Bonne et al. |
| 6,352,874 B1 | 3/2002 | McNeil et al. |
| 6,361,206 B1 | 3/2002 | Bonne |
| 6,383,832 B1 | 5/2002 | Nakabayashi |
| 6,478,974 B1 | 11/2002 | Lebouitz et al. |
| 6,546,812 B2 | 4/2003 | Lewis |
| 6,592,823 B1 * | 7/2003 | Odermatt ............... B01D 53/30 422/83 |
| 6,698,297 B2 | 3/2004 | Gysling |
| 6,879,089 B2 | 4/2005 | Wong et al. |
| 7,280,436 B2 | 10/2007 | Pedersen |
| 7,437,951 B2 | 10/2008 | McDonald et al. |
| 7,556,895 B2 | 7/2009 | Moriya et al. |
| 7,703,339 B2 | 4/2010 | Sulouff, Jr. et al. |
| 7,821,085 B2 | 10/2010 | Suzuki et al. |
| 7,864,403 B2 | 1/2011 | Bita et al. |
| 7,946,505 B2 | 5/2011 | Lynam et al. |
| 8,062,497 B2 | 11/2011 | Witvrouw et al. |
| 8,304,850 B2 * | 11/2012 | Lazarov ............... G01J 5/02 250/338.1 |
| 8,390,121 B2 | 3/2013 | Okumura et al. |
| 8,487,387 B2 | 7/2013 | Lin et al. |
| 8,696,989 B2 | 4/2014 | Esfandyarpour et al. |
| 8,715,514 B2 | 5/2014 | Lee et al. |
| 8,779,781 B2 | 7/2014 | Nguyen et al. |
| 8,806,933 B2 | 8/2014 | Kohno et al. |
| 8,852,513 B1 | 10/2014 | Speer et al. |
| 8,853,798 B2 | 10/2014 | Merz |
| 8,896,073 B2 | 11/2014 | Ponomarev et al. |
| 9,105,479 B2 | 8/2015 | Besling et al. |
| 9,164,052 B1 * | 10/2015 | Speer ............... G01N 27/045 |
| 9,263,500 B2 | 2/2016 | Humbert et al. |
| 9,317,155 B2 | 4/2016 | Magi |
| 9,372,166 B2 | 6/2016 | Daamen et al. |
| 9,448,216 B2 | 9/2016 | Jin et al. |
| 9,459,224 B1 * | 10/2016 | Cheng ............... H01L 28/60 |
| 9,863,901 B2 | 1/2018 | Feyh et al. |
| 2002/0160611 A1 | 10/2002 | Horsley |
| 2002/0166376 A1 | 11/2002 | Kohmura et al. |
| 2003/0039299 A1 | 2/2003 | Horovitz et al. |
| 2003/0079542 A1 | 5/2003 | Bonne et al. |
| 2004/0008041 A1 | 1/2004 | Davis et al. |
| 2004/0084308 A1 | 5/2004 | Cole et al. |
| 2005/0109081 A1 | 5/2005 | Zribi et al. |
| 2005/0218465 A1 | 10/2005 | Cummins |
| 2006/0162466 A1 | 7/2006 | Wargo et al. |
| 2008/0163687 A1 | 7/2008 | Kranz et al. |
| 2008/0194053 A1 | 8/2008 | Huang |
| 2008/0308920 A1 | 12/2008 | Wan |
| 2008/0315332 A1 | 12/2008 | Kaelberer et al. |
| 2009/0218702 A1 | 9/2009 | Beyne et al. |
| 2009/0243003 A1 | 10/2009 | Renna et al. |
| 2010/0173437 A1 | 7/2010 | Wygant et al. |
| 2010/0314740 A1 | 12/2010 | Choi et al. |
| 2011/0031565 A1 | 2/2011 | Marx et al. |
| 2011/0045639 A1 | 2/2011 | Masuko et al. |
| 2011/0108932 A1 | 5/2011 | Benzel et al. |
| 2011/0150261 A1 | 6/2011 | Ho et al. |
| 2011/0298134 A1 | 12/2011 | Williams et al. |
| 2012/0024054 A1 | 2/2012 | Huang et al. |
| 2012/0032283 A1 | 2/2012 | Frey et al. |
| 2012/0144921 A1 | 6/2012 | Bradley et al. |
| 2012/0167392 A1 | 7/2012 | Cherian et al. |
| 2012/0168882 A1 | 7/2012 | Cherian et al. |
| 2012/0171713 A1 | 7/2012 | Cherian et al. |
| 2012/0171774 A1 | 7/2012 | Cherian et al. |
| 2012/0299127 A1 | 11/2012 | Fujii et al. |
| 2012/0304742 A1 | 12/2012 | Cummins |
| 2013/0010826 A1 | 1/2013 | Le Neel et al. |
| 2013/0036806 A1 | 2/2013 | Kohno |
| 2013/0106813 A1 | 5/2013 | Hotelling et al. |
| 2013/0139587 A1 | 6/2013 | Le Neel et al. |
| 2013/0202489 A1 | 8/2013 | Ong et al. |
| 2013/0334620 A1 | 12/2013 | Chu et al. |
| 2013/0344609 A1 | 12/2013 | Mayer et al. |
| 2014/0197500 A1 | 7/2014 | Guillemet et al. |
| 2014/0264655 A1 | 9/2014 | Williams et al. |
| 2014/0264744 A1 | 9/2014 | Chu et al. |
| 2014/0268523 A1 | 9/2014 | Gogoi |
| 2014/0291677 A1 | 10/2014 | Le Neel et al. |
| 2014/0291829 A1 | 10/2014 | Le Neel et al. |
| 2014/0292317 A1 | 10/2014 | Le Neel et al. |
| 2014/0294046 A1 | 10/2014 | Le Neel et al. |
| 2014/0311905 A1 | 10/2014 | Stetter et al. |
| 2014/0353773 A1 | 12/2014 | Loh et al. |
| 2015/0285772 A1 | 10/2015 | Park et al. |
| 2015/0323510 A1 | 11/2015 | Huynh et al. |
| 2016/0018356 A1 | 1/2016 | Shankar et al. |
| 2017/0016866 A1 | 1/2017 | Chey et al. |
| 2017/0066646 A1 | 3/2017 | Cheng et al. |
| 2017/0074815 A1 | 3/2017 | Udrea et al. |
| 2017/0336343 A1 | 11/2017 | Bhat et al. |
| 2017/0370865 A1 | 12/2017 | Samarao et al. |
| 2018/0017513 A1 | 1/2018 | Le Neel et al. |
| 2018/0017536 A1 | 1/2018 | Le Neel et al. |

FOREIGN PATENT DOCUMENTS

| | | |
|---|---|---|
| CN | 1961209 A | 5/2007 |
| CN | 201307027 Y | 9/2009 |
| CN | 201589950 U | 9/2010 |
| CN | 101975751 A | 2/2011 |
| CN | 102680016 A | 9/2012 |
| CN | 102680018 A | 9/2012 |
| CN | 102735716 A | 10/2012 |
| CN | 101788315 B | 11/2012 |
| CN | 102879648 A | 1/2013 |
| CN | 102915993 A | 2/2013 |
| CN | 202770456 U | 3/2013 |
| CN | 103226040 A | 7/2013 |
| CN | 103364455 A | 10/2013 |
| CN | 103512926 A | 1/2014 |
| CN | 103528620 A | 1/2014 |
| CN | 103728350 A | 4/2014 |
| CN | 104792829 A | 7/2015 |
| CN | 105510526 A | 4/2016 |
| CN | 105940295 A | 9/2016 |
| CN | 106164661 A | 11/2016 |
| CN | 207300952 U | 5/2018 |
| JP | 58-106451 A | 6/1983 |
| JP | 4-164242 A | 6/1992 |
| TW | 200531224 A | 9/2005 |
| WO | 2005/087471 A1 | 9/2005 |
| WO | 2015/071337 A1 | 5/2015 |
| WO | 2016/100210 A1 | 6/2016 |

OTHER PUBLICATIONS

Lim et al., "The humidity effect on air flow rates in a critical flow venturi nozzle," *Flow Measurement and Instrumentation* 22(5):402-405, 2011.

Wilson et al., *APTI Course 435 Atmospheric Sampling: Student Manual*, United States Environmental Protection Agency, Research Triangle Park, North Carolina, USA, Sep. 1980, Chapter 3, "Air measuring instruments," pp. 3-1 to 3-49. (61 pages).

World Health Organization, "7 million premature deaths annually linked to air pollution," Mar. 25, 2014, URL=http://www.who.int/mediacentre/news/releases/2014/air-pollution/en/#, download date Jul. 5, 2016, 4 pages.

Raible et al., "Wafer Level Packaging of Micromachined Gas Sensors," *IEEE Sensors Journal* 6(5):2006.

* cited by examiner

GAS SENSORS

BACKGROUND

Technical Field

The present disclosure is directed to gas sensors to detect air quality.

Description of the Related Art

Air pollution is not limited to outdoor air pollution, but also occurs within structures, such as office buildings, homes, and public spaces, like airports. As stale air accumulates within a closed space, concentrations of carbon dioxide and volatile organic compounds (VOCs) may rise to harmful levels.

Air quality is an important factor in maintaining one's health. For example, some cardio-pulmonary ailments are triggered or exacerbated by poor air quality. At higher levels of air pollution, productivity may decrease due to lower levels of oxygen.

High levels of VOCs exist in many buildings constructed using engineered materials that contain glues, dyes, binding agents, adhesives, and the like. Furthermore, cleaning products, solvents, paint and other coatings, furniture, carpeting, and other chemical sources also contribute VOC pollutants. VOCs include such compounds as ethanol, toluene, benzene, formaldehyde, tetrachloroethene (TCE), and methylene chloride.

Green building practices have been introduced in an attempt to limit the use of VOCs and, in some cases, to require a higher outdoor air ventilation rate to prevent accumulation of both VOCs and $CO_2$. Maintaining awareness of the levels of VOCs and $CO_2$ present in ambient air is challenging. While some people are particularly sensitive to VOCs and will experience allergic reactions such as headaches, dizziness, and irritation of the eyes, nose, and throat in a high-VOC environment, most people cannot detect hazardous levels of pollution. Because VOCs and $CO_2$ are both odorless, they are generally difficult to detect, and most buildings today are not equipped with multi-species gas sensors.

BRIEF SUMMARY

The present disclosure is directed to improved gas sensors for detecting air quality, among other things. These gas sensors include a variety of different improvements that can be included alone or in combination with each other to improve gas sensors. These sensors may be indoor air quality sensors and outdoor air quality sensors. These sensors may be in the automotive marketplace, the healthcare marketplace, or any marketplace where air quality is to be monitored.

The present disclosure is directed to various gas sensors that can be carried by a user, such as worn on their clothing, included within an electronic device, attached to a workstation, or incorporated in a room. These gas sensors will detect various species of gases that may be of interest to the user and provide information to the user regarding air quality associated with the user's current environment. For example, the gas sensors could be attached to a user's laptop or computer in an office setting. The gas sensor can display air quality data on displays of the user's electronic devices, such as a tablet, monitor, or mobile telephone. The data may take the form of a statistical summary or a trench chart. The gas sensor may be incorporated in a package with a microprocessor, memory, and other sensors. The package may be directly coupled to the user's electronic device or may be plugged in to an existing port of the electronic device to transmit data from the gas sensor and related circuitry to the display.

BRIEF DESCRIPTION OF THE SEVERAL VIEWS OF THE DRAWINGS

In the drawings, identical reference numbers identify similar elements or acts unless the context indicates otherwise. The sizes and relative positions of elements in the drawings are not necessarily drawn to scale.

DETAILED DESCRIPTION

Figure 1:
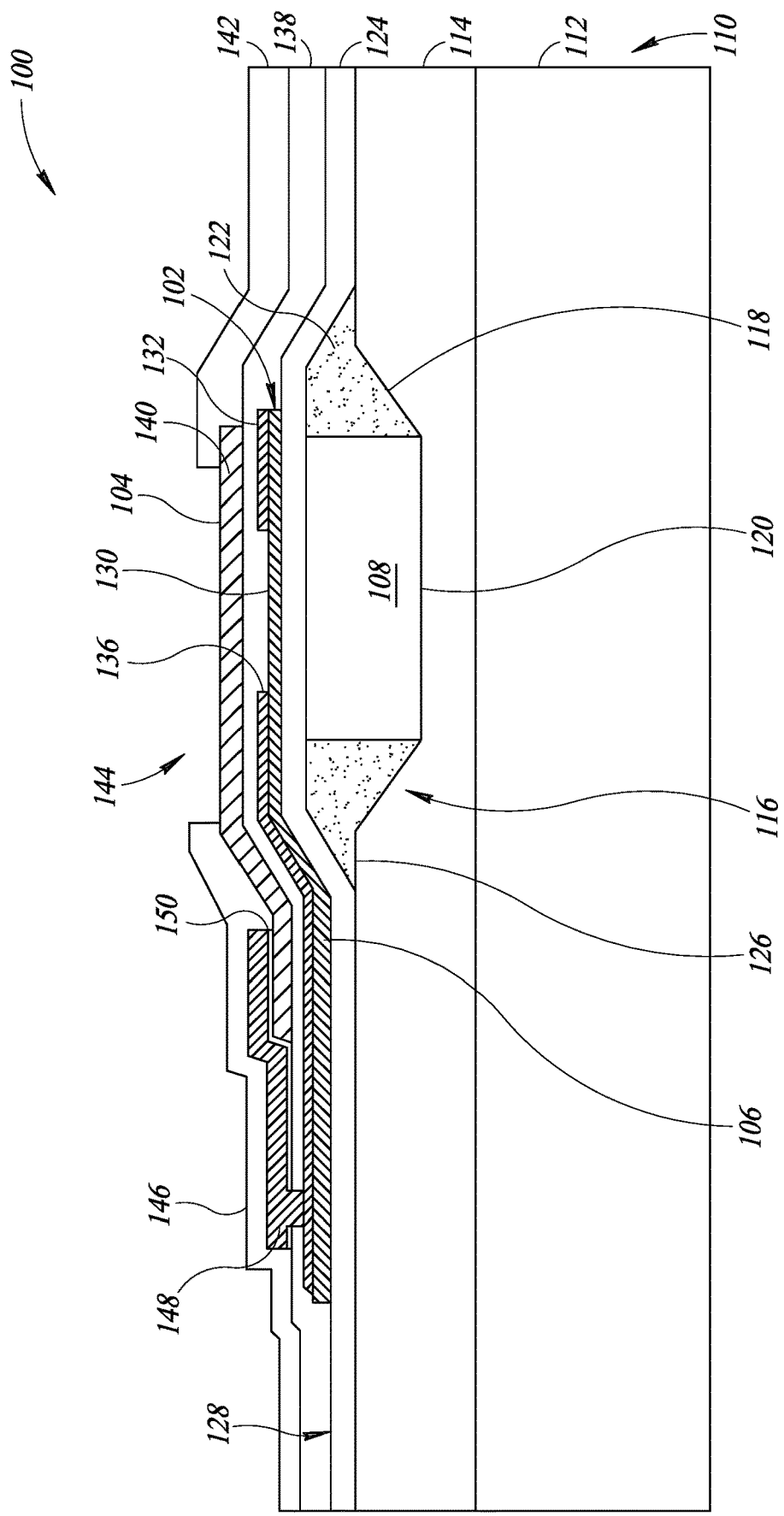
FIG. 1 is a cross-sectional view of a gas sensor having an enlarged heater area according to an embodiment of the present disclosure.

In the following description, certain specific details are set forth in order to provide a thorough understanding of various aspects of the disclosed subject matter. However, the disclosed subject matter may be practiced without these specific details. In some instances, well-known structures and methods of manufacturing electronic devices have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting or glass substrates, whether or not the components are coupled together into a circuit or able to be interconnected. Throughout the specification, the term "layer" is used in its broadest sense to include a thin film, a cap, or the like and one layer may be composed of multiple sub-layers.

The present disclosure is directed to various gas sensors that can be carried by a user, such as worn on their clothing, included within an electronic device, attached to a workstation, or incorporated in a room. These gas sensors will detect various species of gases that may be of interest to the user and provide information to the user regarding air quality associated with the user's current environment. For example, the gas sensors could be attached to a user's laptop or computer in an office setting. The gas sensor can display air quality data on displays of the user's electronic devices, such as a tablet, monitor, or mobile telephone. The data may take the form of a statistical summary or a trench chart. The gas sensor may be incorporated in a package with a microprocessor, memory, and other sensors. The package may be directly coupled to the user's electronic device or may be plugged in to an existing port of the electronic device to transmit data from the gas sensor and related circuitry to the display.

These gas sensors include a plurality of improvements that may be incorporated into gas sensors individually or as combinations. The improvements include an enlarged heater, described in at least FIGS. 1-3, a passive hot plate, described in at least FIGS. 9-10, and a composite heater, described in at least FIGS. 4-7. Each embodiment will be described below and various combinations of these features will be described, however other combinations of these features are envisioned and may be selected based on operation of the particular application of the gas sensor.

FIG. 1 is directed to a gas sensor 100 according to one embodiment of the present disclosure, which includes an enlarged heater 102 that corresponds to an active sensor area 104. Good sensitivity of the gas sensor is achieved with a large heater area of the heater 102, a large active sensor area, a high resistance through a heater interconnect 106, and low power. The active sensor area is where a chemical reaction occurs with elements from an environment. The sensitivity is directly linked to a size of the active sensor area. However, to be sensitive, the area must be heated, which is achieved by power dissipation through a resistance in the heater interconnect using the Joule effect. The power consumption depends on the resistance and gives rise to a compromise between having a larger surface area and a small resistance to reduce the power demand.

The enlarged heater 102 allows for a larger surface for the chemical reaction while maintaining a same resistance (which determines the power consumption). This allows for existing application specific integrated circuits (ASICs) to be used with the design of this gas sensor 100.

The heater 102 is formed above a chamber 108 that is formed in a substrate 110. The substrate 110 may include a silicon layer 112 covered by a first dielectric layer 114. The silicon layer 112 may be 500-600 nanometers. In alternative embodiments, the substrate 110 may be glass. The first dielectric layer may be an oxide that is in the range of 3 microns and 10 microns; it may be deposited or grown. The chamber 108 is formed as a recess 116 in the oxide layer 114 in this embodiment, such as with a photolithography process and an etch. The etch may be a hydrogen fluoride etch that forms the recess having angled walls 118 and a bottom 120 having a 2 micron depth. Other dimensions are envisioned for this embodiment and all other embodiments of this application.

The recess 116 is filled with a polyimide 122 that is covered with a second dielectric layer 124. The polyimide 122 fills the recess and extends past the angled walls 118 to cover a portion 126 of a surface 128 of the first dielectric layer 114. The second dielectric may be a silicon nitride having a thickness in the range of 450 and 550 nanometers.

The heater 102 is formed on the second dielectric layer 124 and may include two layers. For example, a first heater layer 130 is formed on the second dielectric layer 124 and a second heater layer 132 is formed on the first heater layer 130. The first heater layer may be a tantalum aluminum layer having a thickness of around 150 nanometers and the second heater layer may be an aluminum copper layer having a thickness of around 500 nanometers. Tantalum aluminum has a low thermal coefficient that results in a stable resistance. The second heater layer 132 includes an opening 136.

A third dielectric layer 138 is formed on the second heater layer 132 and in the opening 136. The opening corresponds to an enlarged heater area, which is described in more detail with respect to FIGS. 2-3, among others. The heater 102 having a thickness in the range of 500 and 600 nanometers away from the enlarged heater area and a thickness in the range of 100 and 200 nanometers in the enlarged heater area. The third dielectric layer 138 may be a silicon nitride layer that is around 300 nanometers thick.

An active sensor layer 140 is formed on the third dielectric layer 138. This active sensor layer 140 may be a tin oxide that is approximately 100 nanometers thick.

This type of layer may be referred to as a semiconductor metal oxide, SMO. A fourth dielectric layer 142 is formed on the active sensor layer and an opening 144 is formed through the fourth dielectric layer 142 to expose the active sensor area 104.

A conductive layer 146 couples the active sensor layer 140 to the heater 102 through a conductive via 148 through the third dielectric layer 138. A liner 150 may be formed between the conductive layer 146 and the active sensor layer 140. The liner 150 may be titanium tungsten at a thickness of 25 nanometers with the conductive layer 146 being an aluminum copper layer at a thickness of 500 nanometers.

The chamber 108 is formed by etching through the second, third, and fourth dielectric layers in a view now shown in FIG. 1. The polyimide 122 is then etched to form the chamber 108.

Figure 2:
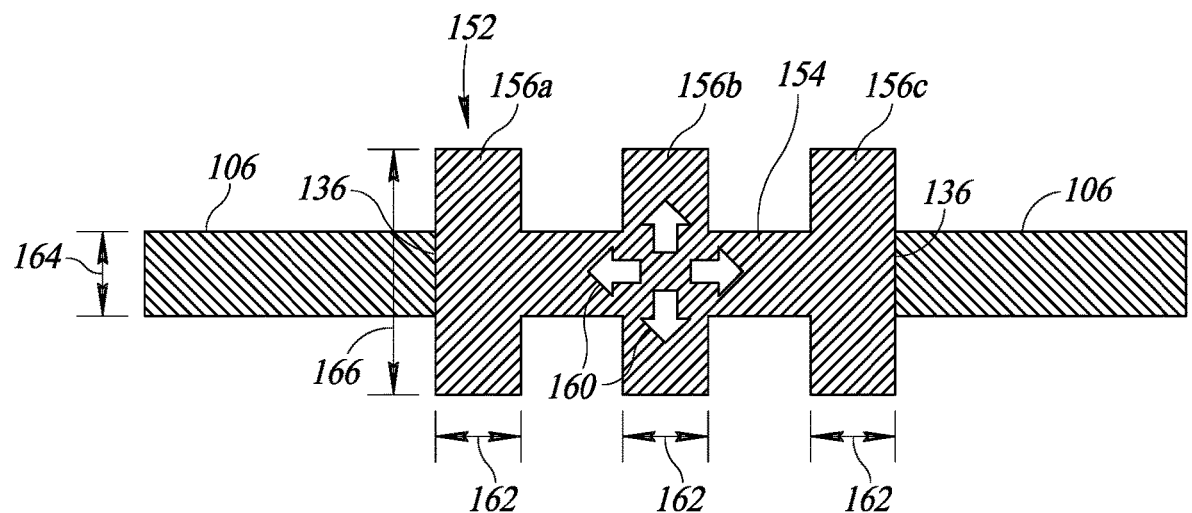
FIGS. 2-3 are alternative top down views of the enlarged heater area of FIG. 1.
Figure 3:
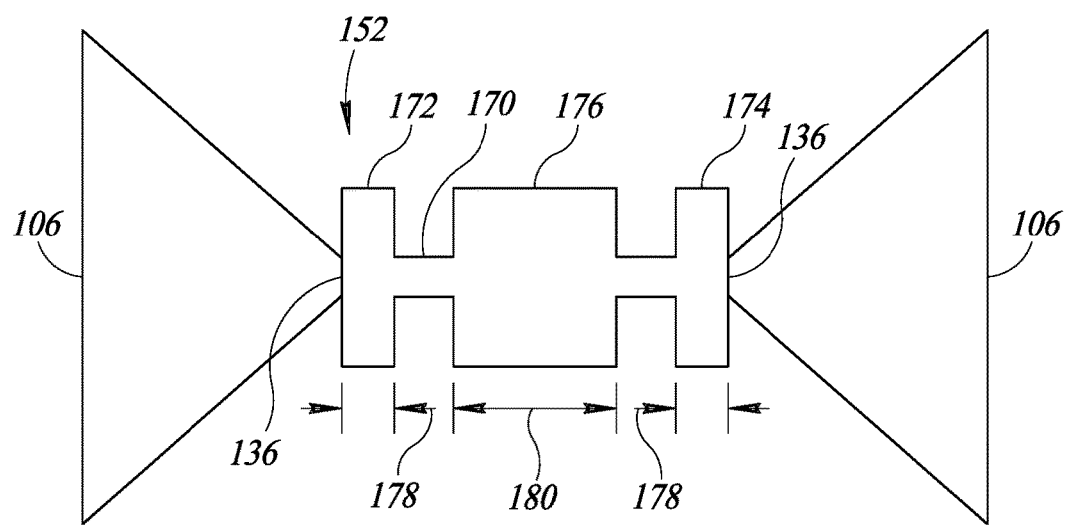

FIGS. 2-3 are top down views of the enlarged heater area. For example, FIG. 2 includes the heater interconnect 106, which is a dual layer of the first and second heater layers. The enlarged heater area 152 corresponds to the opening 136. The heater 102 includes a main extension 154 and a plurality of secondary extensions 156a-156c. Each secondary extension 156a-156c has a same dimension 162. A dimension 164 of the heater interconnect 106 is smaller than a dimension 166 of the secondary extensions. Each of the secondary extensions allows for thermal expansion of the heater.

A total resistance of the heater 102 is ideally in the range of 100 and 150 ohms in order to match demands of an associated ASIC. These secondary extensions are not active from an electrical point of view and as such, no increase in power is used as compared to the main extension alone. The heat generated by the main extension moves outwardly towards the secondary extensions, as shown by arrows 160.

This allows for better heat uniformity in the heater area, which corresponds to better and larger heat uniformity in the active sensor area 104. The larger the heated active sensor area, the more sensitive the gas sensor can be.

A comparison of the main extension only and the main extension plus the secondary extension is as follows where the resistance is the same (100 ohms) with a one milliamp current. The main extension alone has a heater area of 576 micrometers squared where the main extension plus the secondary extensions has a heater area of 1728 micrometers squared. An area of the active sensor area for the main extension alone is 192 micrometers and an area for the active sensor area of the main extension and the secondary extensions is 1700 micrometers squared. A ratio of the active sensor area to the heater area of the main extension alone is 33% while a ratio of the active sensor area to the heater area of the main extension plus the secondary extensions is 98%. This results in a significant increase in sensitivity.

FIG. 3 is an alternative embodiment of the enlarged heater area 152 having the heater interconnects 106 with a different shape than those in FIG. 2. The opening 136 corresponds to the enlarged heater area 152, which is only the first heater layer. The heater includes a first central extension 170, a second and third extension 172, 174 of the same dimensions as each other (dimension 178), and a fourth extension 176 that has different dimensions (dimension 180) than the second and third extensions. The fourth extension 176 is illustrated as a square shape. The fourth extension can be any suitable shape. The fourth extension is larger than the second extension in an area that the extension covers.

Figure 4:
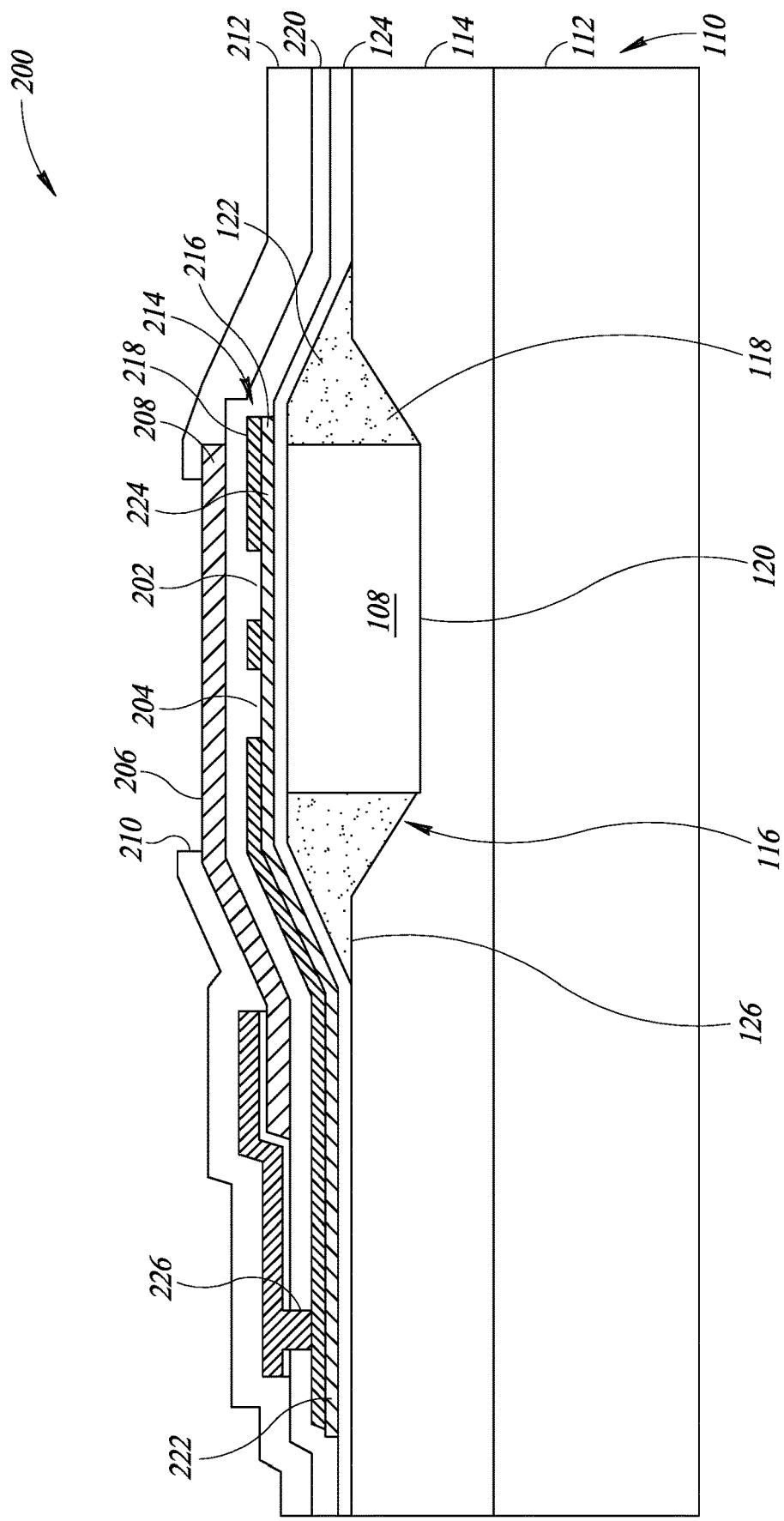
FIG. 4 is a cross-sectional view of a gas sensor having multiple heater openings according to an embodiment of the present disclosure.

FIG. 4 is a cross-sectional view of a gas sensor 200 having multiple heater openings 202 and 204 according to an embodiment of the present disclosure. Two openings will be described; however, embodiments with three or more openings are envisioned. Features of the gas sensor 100 that are similar are referenced using the same reference numbers. In particular, the chamber 108 is formed in the polyimide layer 122, which is supported by the substrate 110.

As mentioned above, sensitivity of such micro-electromechanical gas sensors depends on a size of an active sensor area 206 of an active sensor layer 208. The active sensor area 206 is a portion of the active sensor layer 208 that is exposed through an opening 210 in an upper dielectric layer 212. In order to sense the compounds, the active sensor area is heated by a heater 214 to a temperature that may be in the range of 200 and 500 degrees Celsius. The heat needs to remain localized as to not damage other portions of the gas sensor or other sensors and components included with the gas sensor.

To heat the active sensor layer the heater is heated by power dissipation through resistance and the Joule effect. Power consumption depends on the resistance of the heater. A lower resistance is preferred to maintain low power. The heater is a first conductive layer 216 and a second conductive layer 218. Preferably, the first layer 216 is a tantalum aluminum layer, which allows for power dissipation through resistance while keeping the thermal dissipation stable. The second conductive layer is preferably an aluminum copper layer. Voltage is applied to the heater, power dissipation according to the joule effect starts at room temperature, the joule effect starts increasing the temperature of the heater, the heater resistance tends to increase as the temp increases, and the joule effect is modified due to the resistance change.

In order to improve the heating, openings 202 and 204 are formed in the second conductive layer 218. These openings create a succession of resistances in the heater 214, which heat the active sensor area. The openings 202 and 204 are within bounds of the opening 210, i.e., from a top down view an entire area of the heater is within a boundary of the active sensor area.

The first conductive layer 216 is formed on the dielectric layer 124, which is on the polyimide 122. The second conductive layer 218 is formed directly on the first conductive layer 216. Each of the first and second conductive layers is a consistent thickness throughout in some embodiments. A dielectric layer 220 is formed over the second conductive layer 218.

A first end 222 of the heater 214 is coupled to a contact 226 that receives a voltage and a second end 224 of the heater 214 is coupled to ground. The contact 226 is coupled to the active sensor layer 208 as well.

Heat is generated at the openings 202 and 204 as the openings increase the resistance. The openings 202 and 204 are micron by microns in area, for example 100 by 200 microns square. These openings make the heater more uniform across the active sensor area. There may be three, five, or more of these openings.

Figure 5:
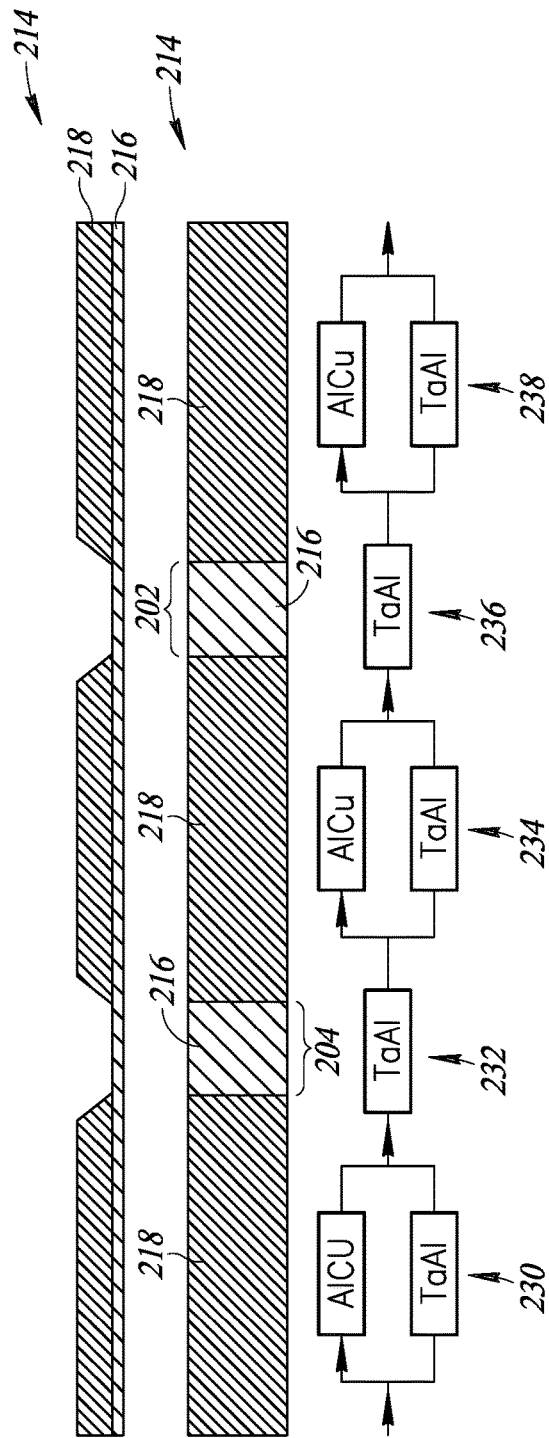
FIG. 5 is an enhanced top and side views of a heater with multiple heater openings that may be incorporated in the gas sensor of FIG. 4.

FIG. 5 is a top down view of a linear version of the heater 214, which includes the first and second openings 202, 204. The heater 214 has five sections 230, 232, 234, 236, 238. The first section 230 is a dual layer of the heater that includes the first and second conductive layers. The third and fifth sections 234 and 238 are also the dual layer. The second and fourth sections 232 and 236 correspond to the openings 214, 216, which have only one layer, the first conductive layer. In the illustrated embodiment, the first layer is tantalum aluminum and the second layer is aluminum copper.

The openings expose the first conductive layer 216. The openings may form vertical sidewalls or may form angled sidewalls. The total resistance of the heater is preferably in the range of 100 and 150 ohms. For the embodiment where the first conductive layer is tantalum aluminum, the resistance is 13.5 ohms/square and the second conductive layer is aluminum copper is 0.025 ohms/square. These openings form two serial resistances under a same current and thus, the same power. The second conductive layer allows the heat to pass through the heater and have a better uniformity. This separates heating locations to cover a larger area of the active sensor layer. The second conductive layer has higher thermal expansion than the first conductive layer, which conducts heat along the heater.

The total resistance of the heater defines the power dissipation as well as the power consumption. By opening the heater at different locations, an equivalent resistance with an enlarged heater surface, which corresponds to a larger active sensor area.

A comparison of a device having only a single heater layer with the device 200 that includes openings in the second conductive layer on the first conductive layer are as follows. A resistance of the single heater device is 100 ohms with a current of one milliamp. The device 200 at a current of one milliamp will have a resistance of 55 ohms.

In the single heater device and the device 200 the heater area is 576 microns squared. In the single heater device the heater is a single layer. In the device 200, the first conductive layer is 240 microns squared and the second conductive layer is 336 microns squared. In the single heater device, the active sensor area is 192 microns squared and in the device 200 the active sensor area is 576 microns squared. The device 200 includes a ratio of 100% of the heater area to the active sensor area.

Figure 6:
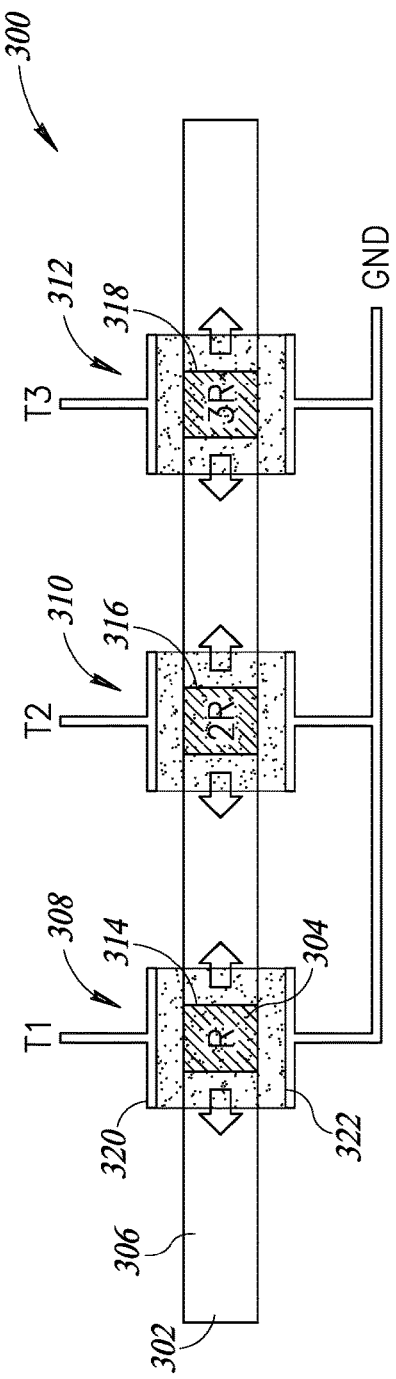
FIG. 6 is an alternative embodiment of the present disclosure that includes a plurality of sensor areas aligned with a single heater layer.

FIG. 6 is an alternative embodiment of the present disclosure that includes a gas sensor 300 having a single heater structure 302 and a plurality of active sensor areas 308, 310, 312. The heater structure 302 includes at least two layers, a first conductive layer 304 that is covered by a second conductive layer 306. The first conductive layer is exposed by openings 314, 316, 318 in the second conductive layer 306.

Each active sensor area overlaps the exposed portions of the first conductive layer through the openings 314, 316, 318. A first end 320 of each active sensor area is coupled to a first terminal. A second end 322 of each active sensor area is coupled to ground. This plurality of active sensor areas may each include an enlarged heater, such as those described in FIGS. 2 and 3 above. Other heater shapes and layer arrangements are described in more detail below and can be incorporated in this gas sensor 300.

Each of the active sensor areas 308, 310, 312 may have a different resistance, which can have power dissipation proportional to the resistance. Each active sensor area can operate at a different specific temperature, with a same power source. Different gases can be detected based on the different operating temperatures.

Figure 7:
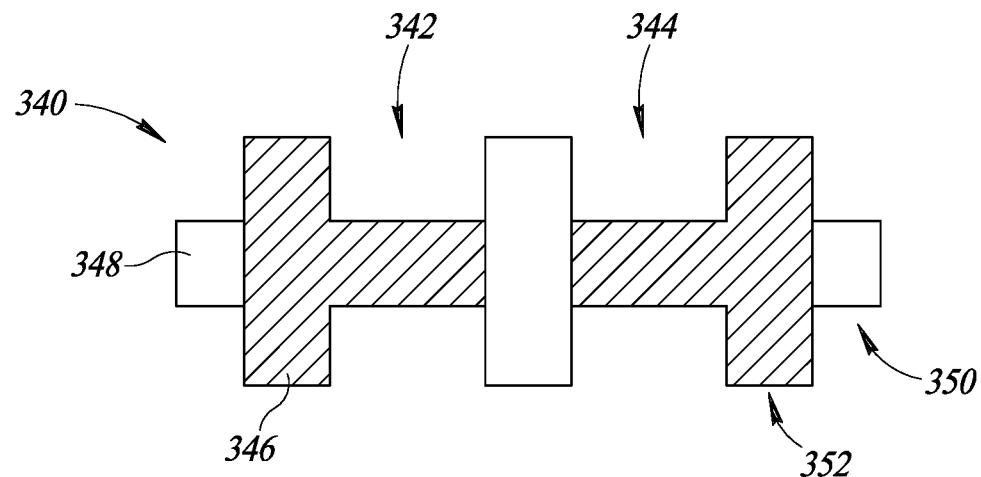
FIG. 7 is an alternative embodiment of the present disclosure having an enlarged heater with a plurality of heater openings.

FIG. 7 is an alternative embodiment of the present disclosure having an enlarged heater 340 with a plurality of openings 342, 344. This heater 340 includes two layers, a first conductive layer 346 that is formed first and a second conductive layer 348 that is formed on the first conductive layer. The heater has a main extension 350 and secondary extensions 352 that add surface area of the heater.

Figure 8:
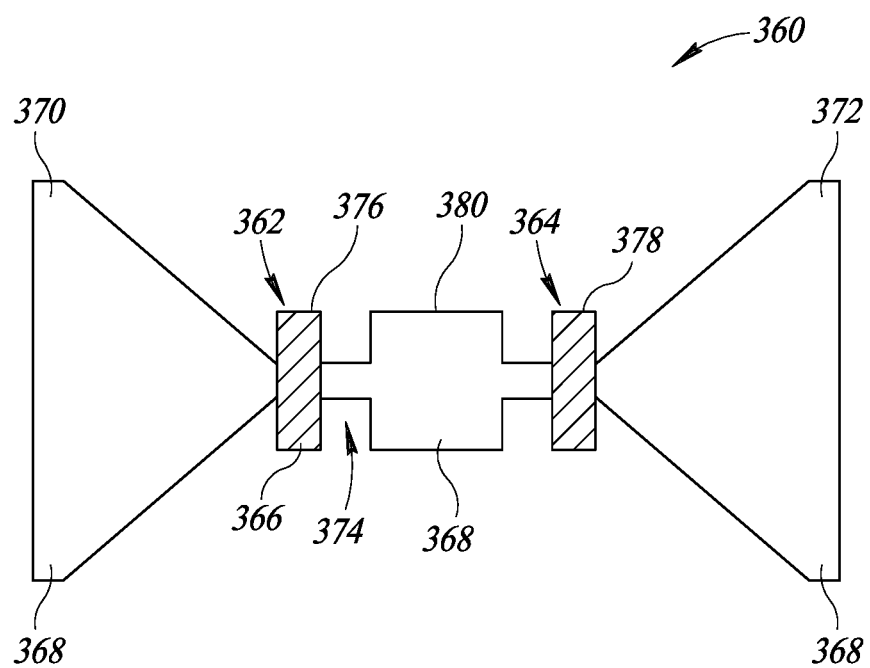
FIG. 8 is an alternative embodiment of the present disclosure having an enlarged heater with a plurality of heater openings.

FIG. 8 is an alternative embodiment of the present disclosure having a heater 360 having a plurality of extensions and a plurality of openings 362, 344 in one of the heater's layers. This heater 360 includes two layers, a first conductive layer 366 that is formed first and a second conductive layer 368 that is formed on the first conductive layer. The heater includes a first terminal end 370 and a second terminal end 372, which each have narrow to couple to a central portion 374 of the heater. First and second extensions 376, 378 that are similar to each other in size and shape overlap and extend from the central portion. A third extension 380 overlaps and extends from the central portion 374. The third extension is square in shape and has a larger area than each of the individual first and second extensions 376, 378. The openings are formed in conjunction with the first and second extensions. Openings may be formed in different locations or with different shapes as dictated by the gas sensor operating conditions or design choices.

The active sensor layer in the embodiments described in this disclosure includes a chemical reaction surface that is in contact with an external environment. High sensitivity of this chemical reaction surface corresponds to a large active area and a high concentration. This chemical reaction surface can detect different gas species based on the temperature at which it is operated. In addition, a concentration of the gas species may vary based on the use of the gas sensor. For example, a maximum of 3 parts per million of ethanol is acceptable in an office environment, which is within a range of 0.1 and 10 parts per million for the office environment. This range is compared to ethanol for a breathalyzer, which may be in the range of 5 and 1,000 parts per million.

The active sensor layer is a thin film gas sensing material that has a structure that supports surface conduction of ambient gas along a substantially straight path. The active sensor layer supports a surface reaction between the ambient gas and a dense, multi-crystalline thin film that is made of a thin film gas sensing material. In one example, the thin film is a tin oxide ($SnO_2$) film of thickness 100 nm. Other gas sensing materials that can be used as the thin film include zinc oxide ($ZnO_2$) and indium oxide ($In_2O_3$). The thin film may be formed by sputter deposition, followed by sintering at a low temperature of 400 C. The resulting thin film is so dense that it is similar to a ceramic. Part or all of the thin film may then be capped with a thin coating of platinum (Pt). The sensitivity of thin film gas sensing materials to various gases that are in ambient air changes as a function of temperature. The platinum coating may assist in transferring heat to the thin film.

The gas sensors of the present disclosure may include a temperature sensor in conjunction with the heater and the active sensor area. The temperature sensor may be formed on a same substrate as the active sensor area. The resistive heater is electronically controlled by a microprocessor according to programmed instructions that may be in a separate package, in a same package or on a same or different substrate than the active sensor area. The microprocessor can to tune the gas sensor to be sensitive to a particular gas. The temperature sensor can be used as a feedback control device for automatically adjusting the resistive heater for a specific gas.

Power is delivered to the resistive heaters via a heater signal line that is driven at a voltage $V_h$. The temperature of each gas sensor is determined by the voltage $V_h$ and a resistance $R_H$ of an associated resistive heater 154. The gas sensor may include multiple active sensor areas that are operated within a different temperature range, such that each of the resistances $R_H$ has different values. This can be accomplished by using different sensing materials in the active sensor areas. For example, a first element may include $SnO_2$ and may be operated within a temperature range of 400 C-500 C, while a second element 150b may include $ZnO_2$ and may be operated in a temperature range of 300 C-350 C. In one embodiment, each temperature sensor is configured as a Wheatstone bridge.

Different gases can be detected by VOC sensors based on material and operating temperature. For example, when a VOC sensor made of $SnO_2$ is heated to an operating temperature of 100 C, it is capable of detecting hydrogen gas. When the $SnO_2$ sensor is heated to an operating temperature of 300 C, it will detect carbon monoxide (CO), and at 400 C, it will detect methane. When a VOC sensor made of $ZnO_2$ is heated to 300 C, it detects nitrogen oxide ($NO_2$). When a VOC sensor made of $InO_2$ is heated to 300 C, it will detect Sulphur dioxide ($SO_2$). Other sensor materials can be substituted for, or used in addition to, $SnO_2$, $ZnO_2$, and $InO_2$ in the VOC sensors.

In one embodiment, the same physical material is heated to different temperatures at different times to sense different gases. In one example, at a first time, the $SnO_2$ layer is heated to about 200 C to detect butane and propane. At a later time, the very same material is heated to about 300 C to detect CO. The local temperature sensor adjacent to the material provides a feedback signal to ensure that the $SnO_2$ material is at the desired temperature for sensing the selected gas.

Figure 9:
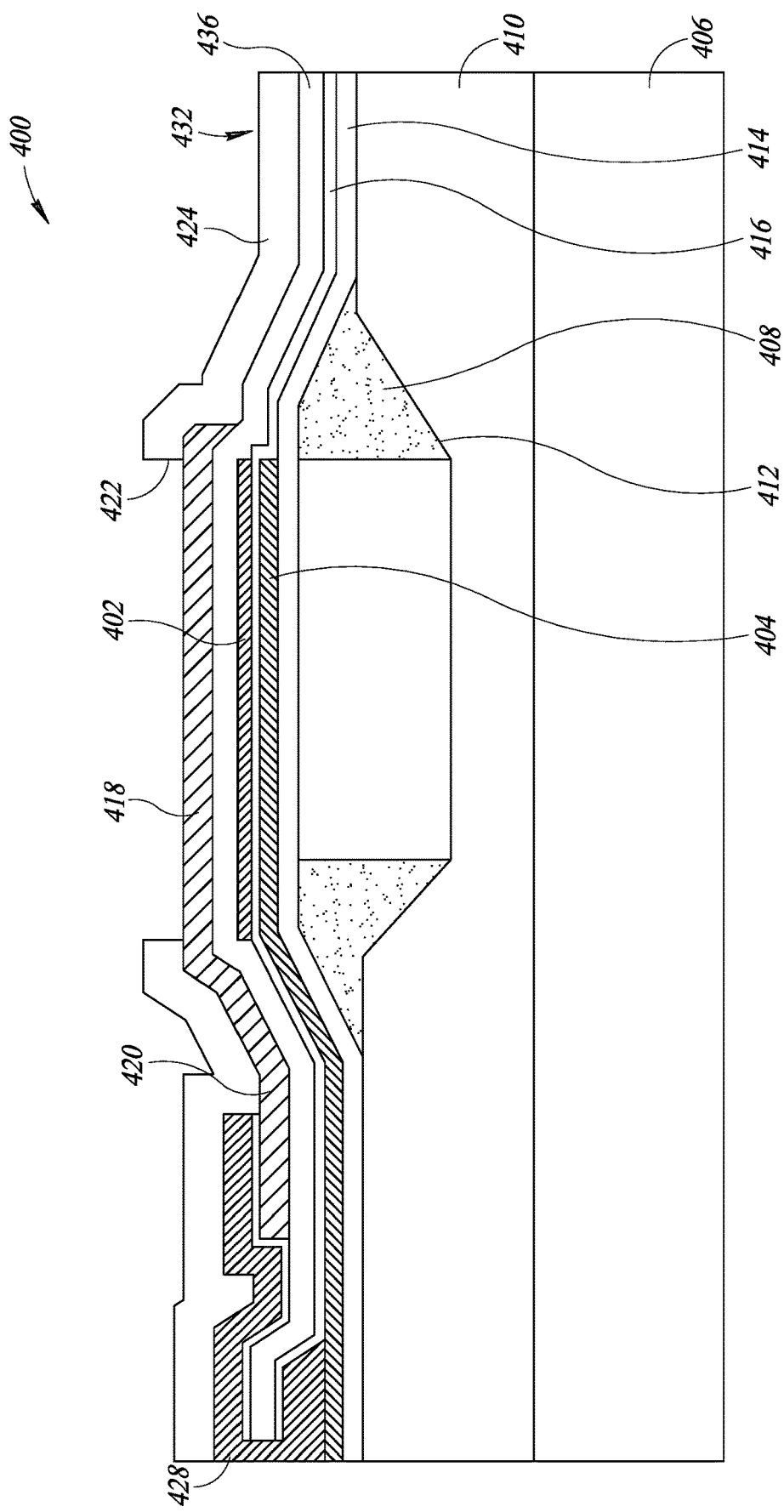
FIG. 9 is a cross-sectional view of an alternative embodiment of a gas sensor of the present disclosure that includes a passive hotplate between a heater and an active sensor area.

FIG. 9 is an alternative embodiment of a gas sensor 400 that includes a passive hotplate 402 aligned with a heater 404. The gas sensor is formed on a substrate 406 that includes a sacrificial material 408. The substrate may include a dielectric layer 410 in which a recess 412 is formed that supports the sacrificial material 408. The sacrificial material may be polyimide of which some may remain in a final version of the gas sensor.

A dielectric layer 414 is formed on the sacrificial material 408 and supports the heater 404. In this embodiment, the heater is illustrated as a single layer; however, there may be additional layers. Another dielectric layer 416 is formed on the heater. The passive hotplate 402 is formed on this dielectric layer 416. The passive hotplate is not electrically coupled to any other components, but is thermally coupled to the heater and to an active sensor area 418. An active sensor layer 420 includes the active sensor area 418, which is exposed by an opening 422 through a dielectric layer 424. The active sensor layer 420 is electrically coupled to the heater 404 with a conductive via 428. A chamber 430 is formed in the sacrificial material 408 through openings (not shown in this view) from a top surface 432 of the sensor 400.

As mentioned above, a single active sensor area can detect different gases at different operating temperatures. Different gasses correspond to different working temperature ranges and peak within their working temperature ranges. Some of the ranges overlap; however, the different peaks (maximum detection temperatures) are different temperatures. Selectivity of the gas sensor can be improved by allowing the sensor to make several measurements at several operating temperatures. The working temperature range of the gas sensor must be less than a difference between the maximum detection temperatures between two gas species. The more precise the working temperature, the more precise the maximum detection will be. Selectivity between species is directly linked to the thermal homogeneity of the active sensor area.

The passive hotplate 402 increases the thermal uniformity of the active sensor area. The passive hotplate 402 is a conductive layer, such as titanium tungsten. A dielectric layer 434 separates the passive hotplate 402 from the active sensor layer 420. This dielectric layer 434 may be silicon nitride.

Figure 10:
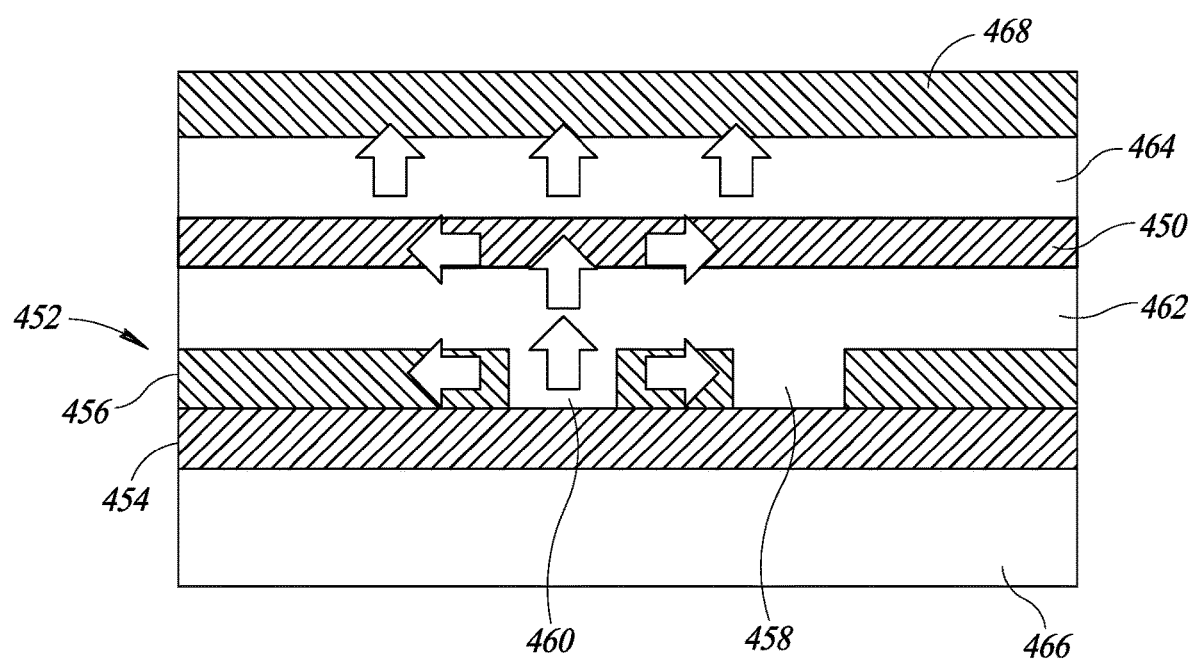
FIG. 10 is a cross-sectional view of a heater having multiple openings and a passive hotplate according to another embodiment of the present disclosure.

FIG. 10 is an alternative embodiment of a passive hotplate 450 that is formed over a heater 452 having a first conductive layer 454 and a second conductive layer 456. Openings 458 and 460 are formed in the second conductive layer 456, which increase the thermal conductivity of the heater. There may be a single opening or two or more openings. A dielectric layer 462 separates the heater from the passive hotplate. Another dielectric layer 464 separates the passive hotplate from an active sensor layer 468.

A material for these passive hotplate layers described in this disclosure are selected based on thermal conductivity. Titanium tungsten has good thermal conductivity and accumulates heat to uniformly transfer it to the active sensor layer. In addition, titanium tungsten has low thermal expansion as compared to other allows and is not subjected to mechanical stresses. The passive hotplate more uniformly distributes heat as compared to a heater that has a smaller surface area than the active sensor area. Such a gas sensor includes two heating approaches that work together. An electro-thermal heat is generated in the heater then thermal conductivity heats the passive hotplate, which transfers the heater more uniformly to the sensor area. The hotplate has a greater surface area than the heater. A surface area of the active sensor area is greater than the heater area and less than or equal to the hotplate surface area.

Comparing a single heater design with a heater and hotplate design results in the following when using a 100 ohm resistor, current of seven milliamps, and a power of 4.9 milli watts, where the heater area for both designs is 576 microns squared. A usable area of the active sensor area is 192 microns squared for a single heater design as compared to a usable area of the active sensor area of 768 microns squared for the hotplate design. A ratio of the heater area to the suable area is 133% for the hotplate design.

Figure 11:
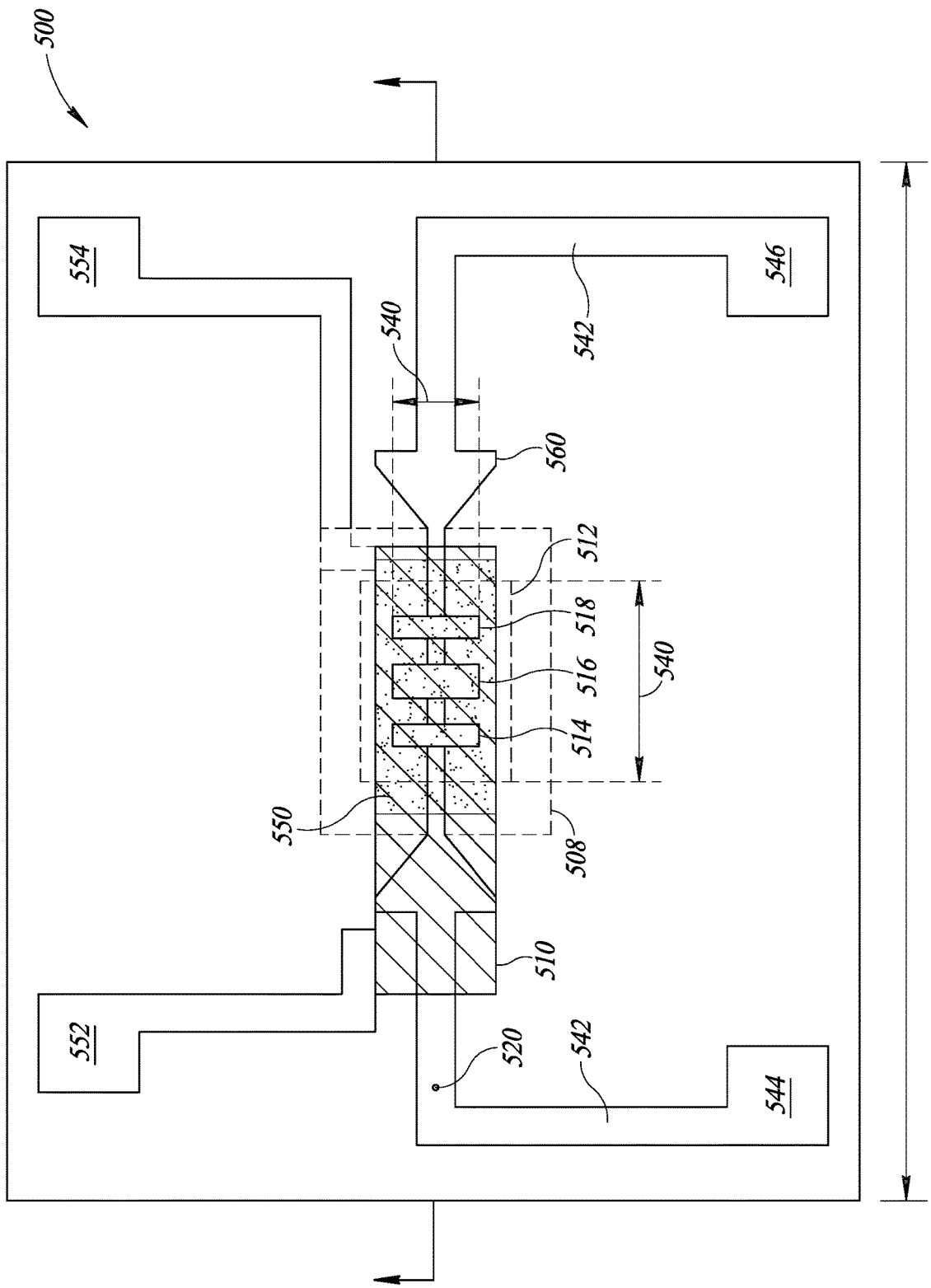
FIGS. 11 and 12 are top and cross-sectional views of a gas sensor according to embodiments of the present disclosure.
Figure 12:
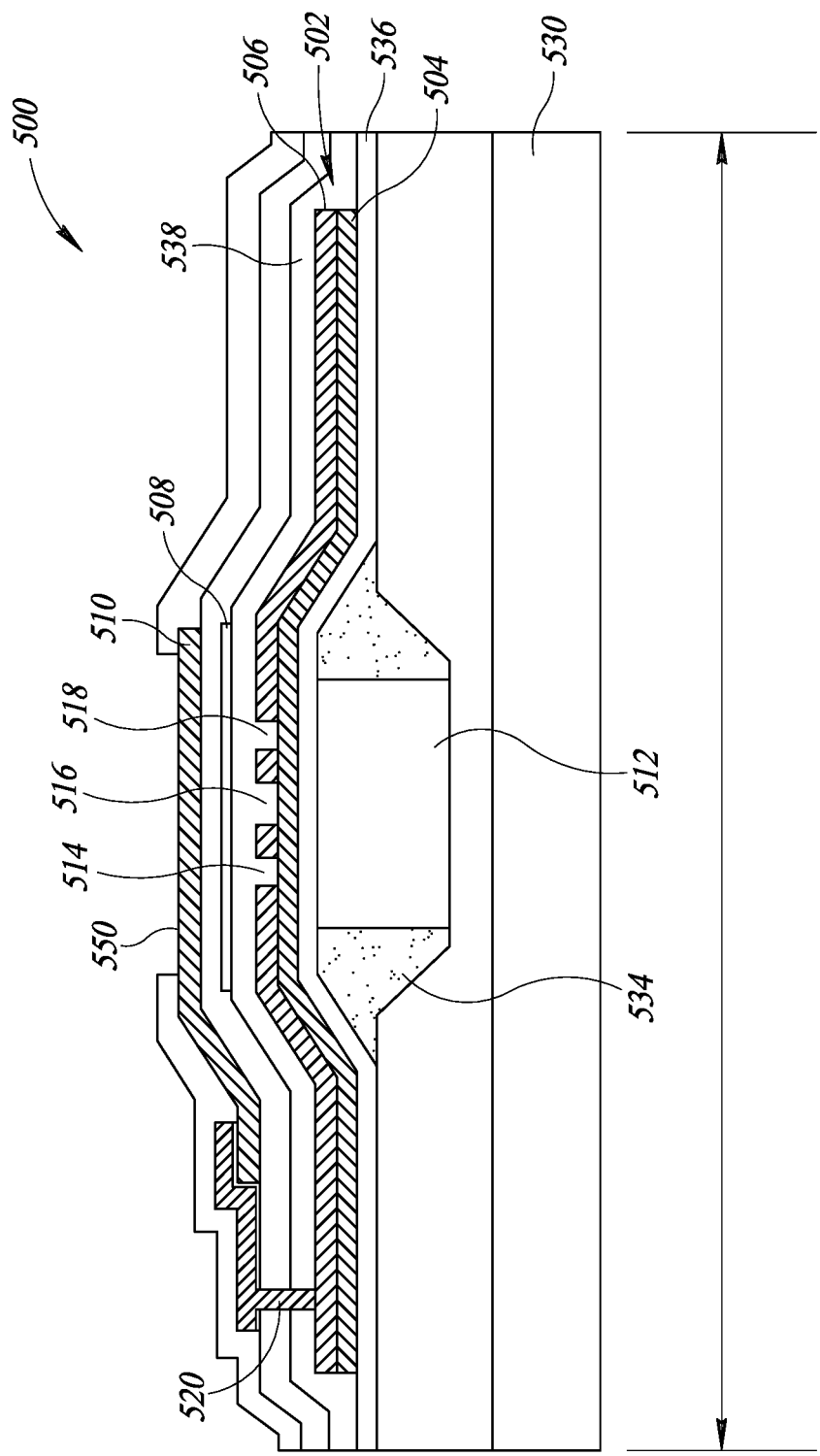

FIGS. 11 and 12 are top and cross-sectional views of a gas sensor 500 that includes a combination of features, such as a two layer heater 502, a passive hotplate 508, and openings 514, 516, 518 in the two layer heater. The gas sensor is formed on a substrate 530 that includes an oxide 532 on the substrate. A recess in which polyimide 534 and a chamber 512 are formed is formed in the oxide layer. A dielectric layer 536 is formed over the chamber, the polyimide, and the oxide.

The heater includes a first layer 504 and a second layer 506. The openings are formed in the second layer 506 of the heater 502. Another dielectric layer 538 is formed on the heater and in the openings. The passive hotplate is formed on the dielectric layer 538 aligned with and overlapping the openings, as can be seen in FIG. 11. A surface area of the hotplate is larger than a surface area of an active portion 540 of the heater 502. The heater includes heater interconnects 542 that are coupled to contact 544, 546. A total area of the die may be 0.4 mm by 0.4 mm.

An active sensor layer 510 is formed on the passive hotplate 508 and includes an active sensor area 550 on which the gas reacts to detect a species of gas. Detection signals are provided by contacts 552, 554 to and from the active sensor area 550.

The active sensor layer 510 is coupled to the heater 502 through via 520. The heater includes triangular sections 560 to increase resistance; however, these are optional based on operational demands of the gas sensor.

Figure 13:
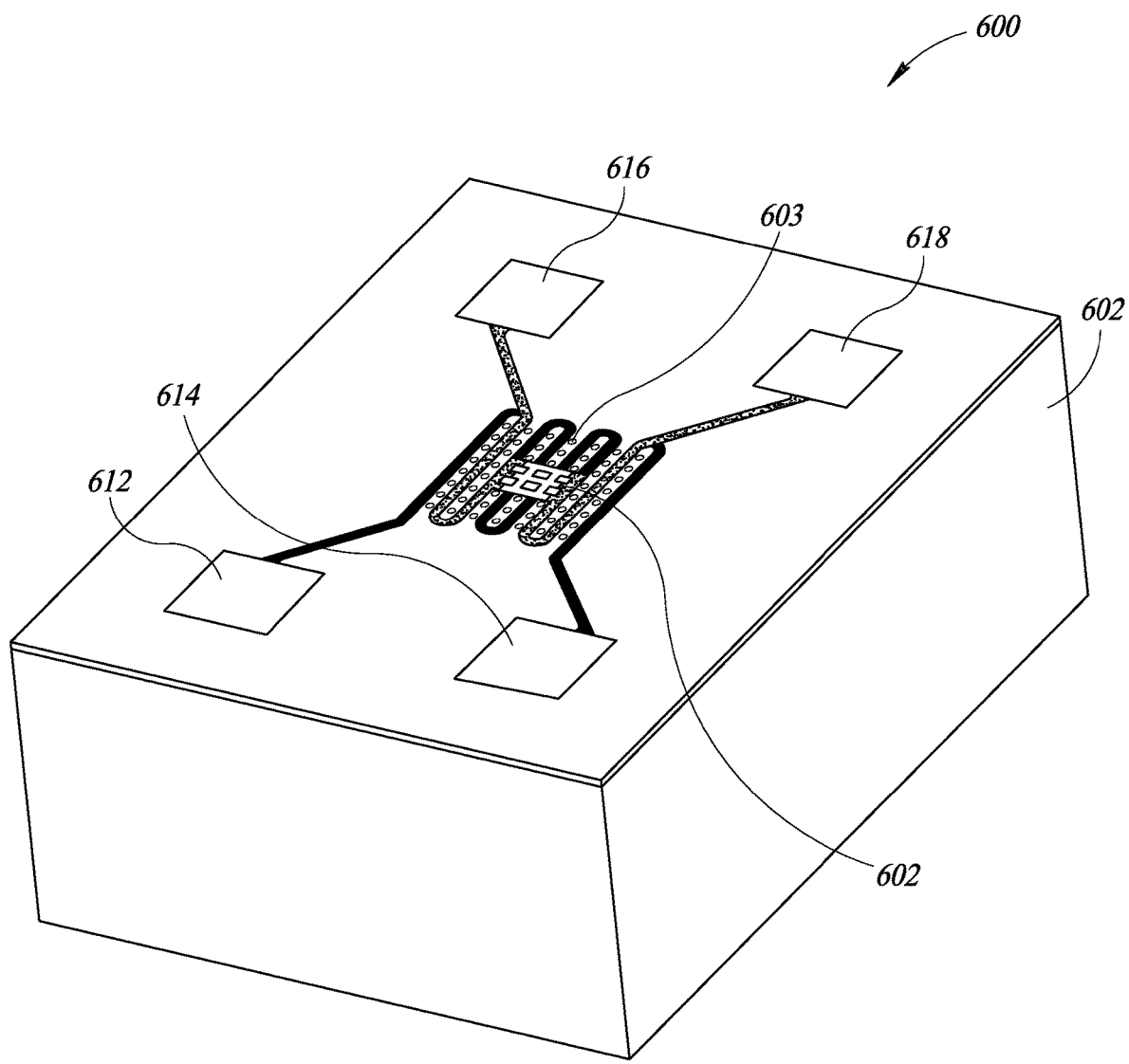
FIGS. 13 and 14 are views of a gas sensor according to another embodiment of the present disclosure.
Figure 14:
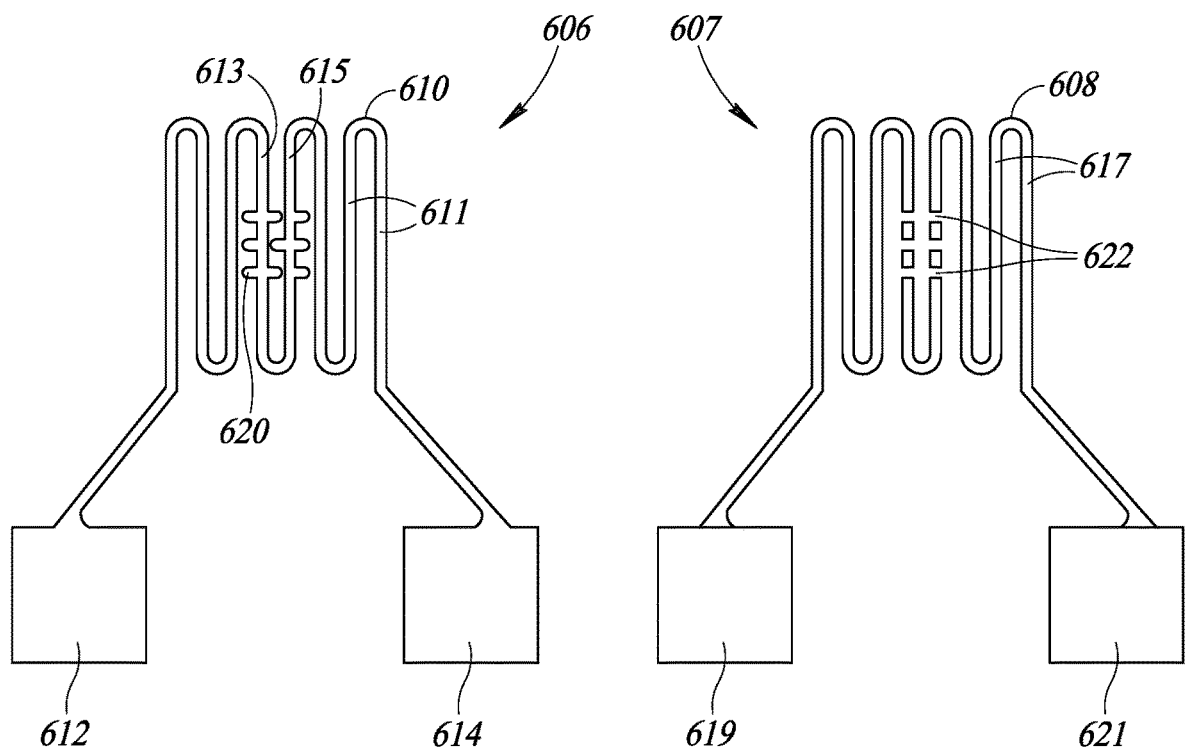
Figure 14:
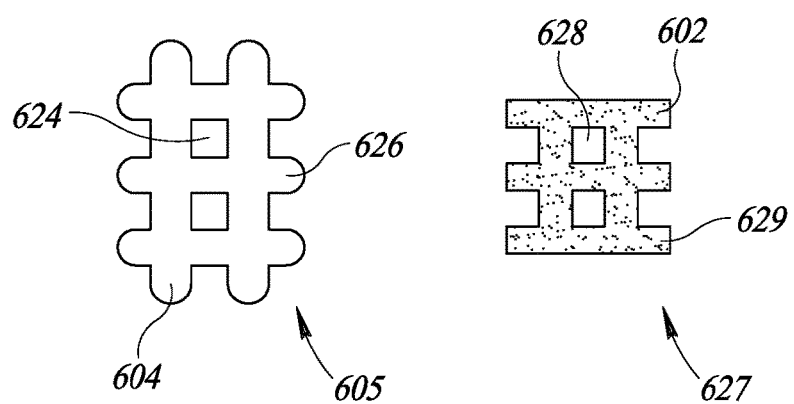

FIGS. 13 and 14 are views of a gas sensor that includes a first heater layer 606, a second heater layer 607, a passive hotplate 605, and an active sensor area 627. The first heater layer 606 is formed on a substrate 602, which may be a semiconductor material, a glass substrate, or other suitable substrate. The second heater layer 607 is formed on top of the first heater layer 606. The second heater layer may be directly on top of and in contact with the first heater layer.

The first heater layer 606 is formed as a serpentine shape with curved ends 610 and straight portions 611. This embodiment includes four curved ends on one side and three curved ends on the other. The curved ends are coupled to ones of the straight portions. The first heater layer includes a first contact 612 and a second contact 614.

The first heater layer 606 includes an enlarged heater area in a central portion that includes extensions 620. The extensions have dimensions that extend transverse to two centrally located straight portions. For example, a first straight portion 613 includes three extensions extending from one side and two extensions extending from the other side. A second straight portion 615 includes a single extension extending from one side towards the first straight portion and three extensions extending from the other side. Different combinations of extensions are available depending on the operational constraints of the end product.

The second heater layer 607 has the same serpentine shape with curved ends 608 and straight portions 617. Two centrally located straight portions include a plurality of openings 622, which cause the heat to be intensified when the first heater layer is activated, in accordance with different embodiments described above. The second heater layer includes contacts 619, 621 that overlap the contacts for the first heater layer. Power is transmitted through both the first and the second heater layer at the same time. In FIG. 13, the combination of the first and second heater layers is shown in black and labeled 601.

The passive hotplate layer 605 is formed above the extensions 620 and the openings 622. The passive hotplate layer includes openings 624 between overlapping portions 604, 626. A surface area covered by the passive hotplate layer is larger than an area of the extensions of the first and second heater layers. The passive hotplate layer is not electrically coupled to any other features. Instead, the passive hotplate layer is thermally coupled to the first and second heater layers.

The active sensor area 627 is part of an active sensor layer 605 (shown in stippling in FIG. 13). The active sensor layer 605 includes contacts 616, 618 at ends that are positioned on an opposite side of the substrate 602 from the contacts 612, 614 for the first and second heater layers. The active sensor area 627 is illustrated without stippling in FIG. 13 to illustrate the active sensor area 627 as compared to the active sensor layer. This active sensor area is exposed to an environment such that the gas species interact with this area for detection by the gas sensor.

These layers are formed over a chamber, the dimensions of which are not visible in these views. Openings 603 are positioned between the serpentine layers to allow for removal of a sacrificial material that supports the layers until the chamber is formed.

The gas sensors can be included in a shared package with humidity and temperature sensors that assist to provide accurate gas readings. All processes used to form these sensors are thin film processes at less than 400 degrees Celsius. These are integrated multi-species gas micro-sensors that are smaller, more accurate, and less expensive than existing air quality sensors. The multi-species gas micro-sensor includes a VOC sensor that includes a conformal thin film less than 0.2 micron thick. Each of the multi-species gas micro-sensor also includes a heater having a low temperature coefficient of resistance.

The present disclosure is directed to a device that includes a substrate, a heater formed on the substrate, the heater having: a first main portion extending in a first direction and a plurality of second portions extending from the first main portion in a second direction that is transverse to the first direction. The device includes an active sensor area above the heater. The heater and the active sensor area are electrically and thermally coupled together.

The device includes a first dielectric layer on the substrate, the heater on the first dielectric layer, a second dielectric layer on the heater, an active sensor layer, and a third dielectric layer on the active sensor layer, the third dielectric layer including an opening that exposes the active sensor area of the active sensor layer. The plurality of second portions includes a first extension having a first area and a second extension having a second area. The first area is greater than the second area. Alternatively, the first area is substantially the same area as the second area.

The substrate includes a chamber formed between the substrate and the first dielectric layer, the heater being aligned over the chamber. The heater includes a first layer and a second layer, the first layer including an opening and the first main portion and the plurality of second portions being formed by the second layer. An area of the opening in the first layer encompasses boundaries of the first main portion and the plurality of second portions.

The present disclosure is also directed to a device that includes a substrate, a heater on the substrate, the heater including a first conductive layer and a second conductive layer on the first conductive layer, the second conductive layer including a first opening and a second opening. The device includes a first active sensor layer on the heater and a first dielectric layer on the first active sensor layer, the first dielectric layer including a third opening that exposes a first active sensor area of the active sensor layer.

The active sensor area is aligned with and positioned over the first and second openings in the second conductive layer. The active sensor layer is coupled to the heater. A second active sensor layer on the heater, the first active sensor layer aligned with the first opening of the second conductive layer and the second active sensor layer aligned with the second opening of the second conductive layer, the first dielectric including a fourth opening that exposes a second active sensor area of the second active sensor layer.

A first end of the first active sensor layer and a first end of the second active sensor layer are coupled together and a second end of the first active sensor layer is coupled to a first terminal and a second end of the second active sensor layer is coupled to a second terminal. The first and second terminals are controlled separately.

The present disclosure is also directed to a device that includes a substrate, a heater on the substrate, a passive heat conductive plate on the heater, an active sensor layer on the passive heat conductive plate, and a first dielectric layer on the active sensor layer, the first dielectric layer including a first opening that exposes an active sensor area. The heater includes a first conductive layer on the substrate and a second conductive layer on the first conductive layer, the second conductive layer including a plurality of second openings that expose a surface of the first conductive layer.

The device includes a chamber in the substrate, the chamber being aligned with the active sensor area. The heater includes a first end, a second end, and a central region, the first and second ends having a first dimension in a first direction, the central region including a plurality of extensions having a second dimension in the first direction, the second dimension being larger than the first dimension. The first conductive layer includes a first terminal, a second terminal, and a central region that extends between the first terminal and the second terminal and has a serpentine shape. The serpentine shape includes a plurality of linear portions coupled together by curved ends. Ones of the plurality of linear portions include protrusions that extend transversely from the linear portions.

A first linear portion is adjacent to a second linear portion, the first linear portion including a plurality of first protrusions and a second linear portion including a plurality of second protrusions. A first linear portion includes first protrusions on a first side of the first linear portion and a second linear portion includes second protrusions on a first side of the second linear portion that faces the first side of the first linear portion. The first protrusions extend toward the second linear portion and the second protrusions extend toward the first protrusion. Ones of the first protrusions are spaced from each other by one of the second protrusions. The first linear portion includes third protrusions that extend from a second side of the first linear portion and the second linear portion includes fourth protrusions that extend from a second side of the second linear portion.

The second conductive layer includes a first terminal, a second terminal, and a central region that extends between the first terminal and the second terminal and has a serpentine shape. The first conductive layer includes a plurality of protrusions in the central region. The second conductive layer includes the plurality of second openings in the central region. The second openings are aligned with the plurality of protrusions. The passive heat conductive plate includes a plurality of third openings.

The passive heat conductive plate includes a first and a section linear portion that are adjacent to each other and extend along a first direction and a third and fourth linear portion that are adjacent to each other and extend along a second direction that is transverse to the first direction. The active sensor layer includes a plurality of third openings in the active sensor area.

The device includes the heater that includes a plurality of extensions, the passive heat conductive plate includes a plurality of second openings, the active sensor layer includes a plurality of third openings in the active sensor area. The plurality of extensions are aligned with the first opening, the plurality of second openings, and the plurality of third openings. The substrate includes a chamber, the plurality of extensions positioned over the chamber.

The present disclosure includes a method that includes forming a heater on a substrate by: forming a first conductive layer on the substrate, forming a second conductive layer on the first conductive layer, forming an active sensor layer on the heater, forming a first dielectric layer on the active sensor layer. The method includes forming an active sensor area by: forming a first opening in the first dielectric layer and reexposing a surface of the active sensor layer. The method includes forming a passive heat conductive hotplate between the heater and the active sensor area of the active sensor layer. The method includes forming a plurality of extensions in the heater, the plurality of extensions aligned with the first opening in the dielectric layer. The method includes forming a plurality of second openings in the second conductive layer.

The method includes forming a recess in the substrate, forming a second dielectric in the recess in the substrate, forming the heater on the second dielectric in the recess, and forming a chamber by removing a first portion of the second dielectric in the recess. The method includes forming the recess including removing a portion of the substrate from a first surface of the substrate and forming the second dielectric layer includes forming the second dielectric layer in the recess and above the first surface of the substrate.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a substrate;
   a heater formed on the substrate, the heater having:
      a first conductive layer including:
         a first main portion extending in a first direction, the first main portion having a first side and a second side opposite to the first side; and
         a plurality of second portions extending from the first main portion in a second direction that is transverse to the first direction, each of the plurality of second portions extending outward from the first side of the first main portion and outward from the second side of the first main portion; and
      a second conductive layer on the first conductive layer, the second conductive layer including an opening that exposes the first main portion and the plurality of second portions; and
   an active sensor layer on the heater.

2. The device of claim 1 wherein the heater and the active sensor layer are coupled together.

3. The device of claim 2, further comprising:
   a first dielectric layer on the substrate, the heater on the first dielectric layer;
   a second dielectric layer on the heater; and
   a third dielectric layer on the active sensor layer, the third dielectric layer including an opening that exposes an active sensor area of the active sensor layer, the active sensor area overlapping the first main portion and the plurality of second portions.

4. The device of claim 1 wherein the plurality of second portions includes a first extension having a first area and a second extension having a second area.

5. The device of claim 4 wherein the first area is greater than the second area.

6. The device of claim 4 wherein the first area is substantially the same area as the second area.

7. The device of claim 1 wherein an area of the opening in the second conductive layer encompasses boundaries of the first main portion and the plurality of second portions.

8. A device, comprising:
   a substrate;
   a heater on the substrate, the heater including:
      a first conductive layer; and
      a second conductive layer directly on the first conductive layer, the second conductive layer including a first opening and a second opening, the first opening and the second opening exposing the first conductive layer;
   a first active sensor layer on the heater, the first active sensor layer being spaced from the first conductive layer by the second conductive layer; and
   a first dielectric layer on the first active sensor layer, the first dielectric layer including a third opening that exposes a first active sensor area of the first active sensor layer, the first active sensor area directly overlying the first opening.

9. The device of claim 8, further comprising a second active sensor layer on the heater, the first dielectric including a fourth opening that exposes a second active sensor area of the second active sensor layer, the second active sensor area directly overlying the second opening.

10. The device of claim 9 wherein a first end of the first active sensor layer and a first end of the second active sensor layer are coupled together and a second end of the first active sensor layer is coupled to a first terminal and a second end of the second active sensor layer is coupled to a second terminal, the first and second terminal are controlled separately.

11. A device, comprising:
   a substrate;
   a heater on the substrate;
   a passive heat conductive plate on the heater, the passive heat conductive plate having a first surface and a second surface opposite to the first surface;
   an active sensor layer on the passive heat conductive plate, the first surface of the passive heat conductive plate facing the active sensor layer, the second surface of the passive heat conductive plate facing the heater, the active sensor layer being made of a gas sensing material; and a first dielectric layer on the active sensor layer, the first dielectric layer including a first opening that exposes an active sensor area of the active sensor layer, the active sensor area being aligned with the heater and the passive heat conductive plate.

12. The device of claim 11 wherein the heater includes a first conductive layer on the substrate and a second conductive layer on the first conductive layer, the second conductive layer including a plurality of second openings that expose a surface of the first conductive layer.

13. The device of claim 12, further comprising a chamber in the substrate, the chamber being aligned with the active sensor area.

14. The device of claim 12 wherein the heater includes a first end, a second end, and a central region, the first and second ends having a first dimension in a first direction, the central region including a plurality of extensions having a second dimension in the first direction, the second dimension being larger than the first dimension.

15. The device of claim 12 wherein the first conductive layer includes a first terminal, a second terminal, and a central region that extends between the first terminal and the second terminal and has a serpentine shape.

16. The device of claim 15 wherein the serpentine shape includes a plurality of linear portions coupled together by curved ends.

17. The device of claim 16 wherein a first linear portion includes first protrusions on a first side of the first linear portion and a second linear portion includes second protrusions on a first side of the second linear portion that faces the first side of the first linear portion, the first protrusions extend toward the second linear portion and the second protrusions extend toward the first protrusion.

18. The device of claim 17 wherein ones of the first protrusions are spaced from each other by one of the second protrusions, the first linear portion includes third protrusions that extend from a second side of the first linear portion and the second linear portion includes fourth protrusions that extend from a second side of the second linear portion.

19. The device of claim 15 wherein the second conductive layer includes a first terminal, a second terminal, and a central region that extends between the first terminal and the second terminal and has a serpentine shape.

20. The device of claim 19 wherein the first conductive layer includes a plurality of protrusions in the central region.

21. The device of claim 20 wherein the second conductive layer includes the plurality of second openings in the central region, the second openings are aligned with the plurality of protrusions.

22. The device of claim 21 wherein the passive heat conductive plate includes a plurality of third openings.

23. The device of claim 11 wherein:
the heater includes a plurality of extensions;
the passive heat conductive plate includes a plurality of second openings;
the active sensor layer includes a plurality of third openings in the active sensor area.

24. The device of claim 23 wherein the plurality of extensions are aligned with the first opening, the plurality of second openings, and the plurality of third openings, the substrate includes a chamber, the plurality of extensions being positioned over the chamber.

25. The device of claim 1 wherein the first conductive layer and the second conductive layer are in direct contact with each other.

26. The device of claim 8 wherein the active sensor layer is made of a gas sensing material.

* * * * *